United States Patent
Kositprapa et al.

(10) Patent No.: US 8,309,125 B2
(45) Date of Patent: *Nov. 13, 2012

(54) PHARMACEUTICAL FORMULATION CONTAINING A BIGUANIDE AND A THIAZOLIDINEDIONE DERIVATIVE

(75) Inventors: Unchalee Kositprapa, Davie, FL (US); Avinash Nangia, Weston, FL (US); John Cardinal, Tamarac, FL (US); Robert I. Goldfarb, Golden Beach, FL (US)

(73) Assignee: Watson Pharmaceuticals, Inc., Corona, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 12/835,945

(22) Filed: Jul. 14, 2010

(65) Prior Publication Data

US 2010/0316708 A1 Dec. 16, 2010

Related U.S. Application Data

(63) Continuation of application No. 10/664,803, filed on Sep. 19, 2003, now Pat. No. 7,785,627.

(60) Provisional application No. 60/412,180, filed on Sep. 20, 2002, provisional application No. 60/412,181, filed on Sep. 20, 2002.

(51) Int. Cl.
*A61K 9/28* (2006.01)
*A61K 31/4439* (2006.01)
*A61K 9/22* (2006.01)
*A61P 3/10* (2006.01)
*A61P 3/04* (2006.01)

(52) U.S. Cl. ....... 424/465; 424/468; 424/484; 427/2.14; 514/342

(58) Field of Classification Search .......... 424/484, 424/465, 468; 427/2.14; 514/342
See application file for complete search history.

(56) References Cited

U.S. PATENT DOCUMENTS

| | | |
|---|---|---|
| 3,174,901 A | 3/1965 | Sterne |
| 3,621,097 A | 11/1971 | Scott |
| 3,845,770 A | 11/1974 | Theeuwes et al. |
| 3,916,899 A | 11/1975 | Theeuwes et al. |
| 3,960,949 A | 6/1976 | Ahrens et al. |
| 4,034,758 A | 7/1977 | Theeuwes |
| 4,058,122 A | 11/1977 | Theeuwes et al. |
| 4,077,407 A | 3/1978 | Theeuwes et al. |
| 4,080,472 A | 3/1978 | Bohuon |
| 4,160,020 A | 7/1979 | Ayer et al. |
| 4,166,800 A | 9/1979 | Fong |
| 4,220,648 A | 9/1980 | Youngdale |
| 4,389,330 A | 6/1983 | Tice et al. |
| 4,687,777 A | 8/1987 | Meguro et al. |
| 4,783,337 A | 11/1988 | Wong et al. |
| 4,839,177 A | 6/1989 | Colombo et al. |
| 4,857,336 A | 8/1989 | Khanna et al. |
| 4,857,337 A | 8/1989 | Miller et al. |
| 4,891,223 A | 1/1990 | Ambegaonkar et al. |
| 4,900,558 A | 2/1990 | Barry et al. |
| 4,968,507 A | 11/1990 | Zentner et al. |
| 5,055,306 A | 10/1991 | Barry et al. |
| 5,200,194 A | 4/1993 | Engren et al. |
| 5,294,770 A | 3/1994 | Riddle et al. |
| 5,356,913 A | 10/1994 | Colca |
| 5,376,771 A | 12/1994 | Roy |
| 5,478,852 A | 12/1995 | Olefsky et al. |
| 5,602,133 A | 2/1997 | Antonucci et al. |
| 5,658,474 A | 8/1997 | Geerke |
| 5,681,584 A | 10/1997 | Savastano et al. |
| 5,698,220 A | 12/1997 | Cardinal et al. |
| 5,719,188 A | 2/1998 | Colca |
| 5,840,335 A | 11/1998 | Wenzel et al. |
| 5,858,398 A | 1/1999 | Cho |
| 5,859,037 A | 1/1999 | Whitcomb |
| 5,916,584 A | 6/1999 | O'Donoghue et al. |
| 5,948,440 A | 9/1999 | Arora et al. |
| 5,952,356 A | 9/1999 | Ikeda et al. |
| 5,955,106 A | 9/1999 | Moeckel et al. |
| 5,965,584 A | 10/1999 | Ikeda et al. |
| 6,011,049 A | 1/2000 | Whitcomb |
| 6,031,004 A | 2/2000 | Timmins et al. |
| 6,056,977 A | 5/2000 | Bhagwat et al. |
| 6,099,859 A | 8/2000 | Cheng et al. |
| 6,099,862 A | 8/2000 | Chen et al. |
| 6,153,632 A | 11/2000 | Rieveley |
| 6,166,042 A | 12/2000 | Ikeda et al. |
| 6,166,043 A | 12/2000 | Ikeda et al. |
| 6,172,090 B1 | 1/2001 | Ikeda et al. |
| 6,191,162 B1 | 2/2001 | Byrd et al. |
| 6,248,363 B1 | 6/2001 | Patel et al. |
| 6,284,275 B1 | 9/2001 | Chen et al. |
| 6,291,495 B1 | 9/2001 | Rieveley |
| 6,296,874 B1 | 10/2001 | Cutie et al. |

(Continued)

FOREIGN PATENT DOCUMENTS

AU 1272788 A1 9/1988

(Continued)

OTHER PUBLICATIONS

Hotta, Yutaka, Diabetes Update, No. 10, pp. 68-77, 1994, and English translation.*
ADA Professional Section Member Supplement 047 and 0503-506 (Poster) p. A110; A117.
Abdallah et al, Preparation and evaluation of Metformin Hydrochloride Controlled-Release Tablets, STP Pharma 4(1) pp. 15-20, 1988.
Karttunen, P. et al., International Journal of Clinical Pharmacology, Therapy and Toxicology, "The pharmacokinetics of metformin a comparison of the properties of a rapid release and a sustained-release preparation" vol. 21, No. 1—1983. pp. 31-36.

(Continued)

*Primary Examiner* — Aradhana Sasan
(74) *Attorney, Agent, or Firm* — Florek & Endres PLLC

(57) ABSTRACT

A pharmaceutical dosage form comprising a controlled release component comprising an antihyperglycemic drug in combination with a second component comprising a thiazolidinedione derivative is herein disclosed and described.

7 Claims, No Drawings

U.S. PATENT DOCUMENTS

| | | | |
|---|---|---|---|
| 6,329,403 B1 | 12/2001 | Odaka et al. | |
| 6,342,249 B1 | 1/2002 | Wong et al. | |
| 6,383,471 B1 | 5/2002 | Chen et al. | |
| 6,403,121 B1 | 6/2002 | Adjei et al. | |
| 6,451,342 B2 | 9/2002 | Adjei et al. | |
| 6,475,521 B1 | 11/2002 | Timmins et al. | |
| 6,495,162 B2 | 12/2002 | Cheng et al. | |
| 6,524,621 B2 | 2/2003 | Adjei et al. | |
| 6,596,314 B2 | 7/2003 | Wong et al. | |
| 6,599,284 B2 | 7/2003 | Faour | |
| 6,660,300 B1 | 12/2003 | Timmins et al. | |
| 6,780,432 B1 | 8/2004 | Cutie et al. | |
| 6,790,459 B1 | 9/2004 | Cheng et al. | |
| 6,838,093 B2 | 1/2005 | Flanner et al. | |
| 6,866,866 B1 | 3/2005 | Chen et al. | |
| 7,071,181 B2 | 7/2006 | Davis et al. | |
| 7,374,779 B2 | 5/2008 | Chen et al. | |
| 7,785,627 B2* | 8/2010 | Kositprapa et al. | 424/484 |
| 7,919,116 B2 | 4/2011 | Chen et al. | |
| 7,959,946 B2* | 6/2011 | Kositprapa et al. | 424/473 |
| 2001/0024659 A1 | 9/2001 | Chen et al. | |
| 2001/0046515 A1 | 11/2001 | Adjei et al. | |
| 2002/0064556 A1 | 5/2002 | Cheng et al. | |
| 2002/0071866 A1 | 6/2002 | Geerke | |
| 2003/0077297 A1 | 4/2003 | Chen et al. | |
| 2003/0113371 A1 | 6/2003 | Dhawan et al. | |
| 2003/0118647 A1 | 6/2003 | Seth | |
| 2003/0118649 A1 | 6/2003 | Gao et al. | |
| 2003/0224046 A1 | 12/2003 | Rao et al. | |
| 2004/0081697 A1 | 4/2004 | Lewis et al. | |
| 2004/0092531 A1 | 5/2004 | Chizh et al. | |
| 2005/0074490 A1 | 4/2005 | Lin et al. | |
| 2005/0226928 A1* | 10/2005 | Lodin et al. | 424/469 |
| 2005/0249809 A1* | 11/2005 | Lodin et al. | 424/468 |
| 2006/0008525 A1 | 1/2006 | Chen et al. | |
| 2006/0034922 A1 | 2/2006 | Cheng et al. | |
| 2006/0057202 A1 | 3/2006 | Antarkar et al. | |
| 2006/0141023 A1 | 6/2006 | Trehan et al. | |
| 2006/0141128 A1 | 6/2006 | Ohkouchi et al. | |
| 2006/0204578 A1 | 9/2006 | Vergez et al. | |
| 2006/0286168 A1 | 12/2006 | Koike et al. | |

FOREIGN PATENT DOCUMENTS

| | | |
|---|---|---|
| CN | 1582928 | 2/2005 |
| EP | 0 169 105 | 1/1986 |
| EP | 0283 369 | 9/1988 |
| EP | 0 381 181 | 8/1995 |
| EP | 0 749 751 | 12/1996 |
| EP | 0 753 298 | 11/2001 |
| EP | 0 781 129 | 7/2003 |
| EP | 1 588 708 A1 | 10/2005 |
| WO | WO 93/03724 | 3/1993 |
| WO | WO9608243 | 3/1996 |
| WO | WO 96/09823 | 4/1996 |
| WO | WO 98/11879 | 3/1998 |
| WO | WO 98/55107 | 12/1998 |
| WO | WO 99/47125 | 9/1999 |
| WO | WO 99/47128 | 9/1999 |
| WO | WO 99/55320 | 11/1999 |
| WO | WO 00/28989 | 5/2000 |
| WO | WO 00/72827 | 12/2000 |
| WO | WO 01/35940 | 5/2001 |
| WO | WO 01/35941 | 5/2001 |
| WO | WO 01/47498 | 7/2001 |
| WO | WO 01/74336 | 10/2001 |
| WO | WO 01/82875 | 11/2001 |
| WO | WO 02/11702 | 2/2002 |
| WO | WO 02/28181 | 4/2002 |
| WO | WO 03/004009 | 1/2003 |
| WO | WO 03/035029 | 5/2003 |
| WO | WO 03/045355 | 6/2003 |
| WO | WO 03/047529 | 6/2003 |
| WO | WO03105809 | 12/2003 |
| WO | WO 2004/006921 | 1/2004 |
| WO | WO2004026241 | 4/2004 |
| WO | WO2004045608 | 6/2004 |
| WO | WO 2004/067001 | 8/2004 |
| WO | WO 2005/063226 | 7/2005 |
| WO | WO 2005/110405 | 11/2005 |

OTHER PUBLICATIONS

Pentikainen, P.J., International Journal of Clinical Pharmacology, Therapy and Toxicology, "Bioavailability of metformin. Comparison of solution, rapidly dissolving tablet, and three sustained release products", vol. 24, No. 4—1986, pp. 213-220.

Finnish Monograph of the Diformin(R), Retard tablet, with English translation. O.J. Lucis, MD, Ph.D., MSC, Canada Medical Association J. Pharmacologic Update "The status of metformin in Canada" vol. 128, Jan. 1, 1983, pp. 24-26.

Belcher, et al., Experiment and Clinical Endrocrinology & Diabetes, "Safety and tolerability of pioglitazone" Suppl. 2 (2000) pp. 267-273.

Einhorn, et al., Clinical Therapeutics "Pioglitazone Hydrochloride in Combination with Metformin in the Treatment of Type 2 Diabetes Mellitus: A Randomized, Placebo-Controlled Study", vol. 22, No. 12, 2000 pp. 1395-1413.

National Institute for Clinical Excellence Technology Appraisal Guidance—No. 21, "Guidance on the Use of Pioglitazone for Type 2 Diabetes Mellitus" Mar. 2001. pp. 1-13.

The Pharmaceutical Journal, vol. 265, No. 7122, p. 710 Nov. 11, 2000 Clinical (abstract only).

ADA Professional Section Member Supplement 047 and 0503-506 (Poster) p. A110; A117, Jun. 1999.

Clinician Reviews, "Insulin-Sensitizing Diabetes Agent" Sep. 1999. Product Labeling for Glucophage(R) XR (Jul. 2002).

ACTOS(R) product label, Physician's Desk Reference, 55th Edition, pp. 3171-3175.

An opposition filed in Costa Rica against a related application, 2008.

A translation of the opposition filed in Costa Rica against a related application, 2008.

A response to the opposition filed in Costa Rica against a related application, 2008.

A translation of the response to the opposition filed in Costa Rica against a related application, 2008.

An opposition filed in Chile against a related application, 2008.

A translation of the opposition filed in Chile against a related application, 2007.

A response to the opposition filed in Chile against a related application, 2008.

A translation of the response to the opposition filed in Chile against a related application, 2008.

An English translation of an opposition filed in Columbia against a related application, 2008.

A response to the opposition filed in Columbia against a related application (in Spanish), 2009.

An English translation of a response to the opposition filed in Columbia against a related application, 2009.

A search report from the Georgian Patent Office (and English translation) for a related application, 2008.

An Office Action from the Ukrainian Patent Office (and English translation) for a related application, 2009.

Inzucchi, S. et al., Efficacy of Metabolic Effects of Metformin and Troglitazone in type II diabetes mellitus; N. Engl. J Med. Mar. 26, 1998; 338(13): 867-72.

Fonseca, V., et al., Effect of Metformin and Rosiglitazone combination therapy in patients with type II diabetes mellitus; Apr. 5, 2000; 283(13): 1695-702.

Egger M., et al., Risk of Adverse Effects of Intensified Treatment in Insulin-Dependent Diabetes Mellitus: A Meta-Analysis; Diabetic Med. Nov. 1997; 14 (11): 919-28.

Dailey, GE., Glyburide/Metformin Tablets: A New Therapeutic Option for the Management of Type 2 Diabetes. Expert Opinion Pharmacotherapy (2003) 4(8): 1417-30. Review (Abstract Only).

Bailey, CJ, et al. Avandamet: Combined Metformin-Rosiglitazone Treatment for Insulin Resistance in Type 2 Diabetes, Int J Clin Pract Sep. 2004 58(9): 867-76.

Campbell RK et al., Metformin: A New Oral Biguanide, Clin Ther May-Jun. 1996; 18(3): 360-71.

Davidson, MB, et al., An Overview of Metformin in the Treatment of Type 2 Diabetes Mellitus, Am J Med. Jan. 1997; 102(1):99-110.

Dunn, CJ, et al., Metformin. A Review of its Pharmacological Properties and Therapeutic Use in Non-Insulin-Dependent Diabetes Mellitus, Drugs May 1995; 49(5):721-49.

Zimmer, B., Supplementary European Search Report, EP 03 75 4689, May 6, 2010, European Patent Office 80298 Munich, Germany.

Koski, R.R., Practical Review of Oral Antihyperglycemic Agents for Type 2 Diabetes Mellitus, The Diabetes Educator 32 (6) 869-876 (Nov./Dec. 2006).

Jagoe, D., International Search Report, PCT/US03/29292, Apr. 26, 2004, ISA/US, Commissioner for Patents, P.O. Box 1450, Alexandria Virginia 22313-1450.

Jagoe, D., International Preliminary Examination Report, PCT/US03/29292, Jan. 4, 2005, IPEA/US, Commissioner for Patents, P.O. Box 1450, Alexandria Virginia 22313-1450.

Joynes. R.M., International Search Report, PCT/US04/04112, Aug. 12, 2004, ISA/US, Commissioner for Patents, P.O. Box 1450, Alexandria Virginia 22313-1450.

Nickitas-Etienne, A. International Preliminary Report on Patentability, PCT/US2004/004112, Feb. 28, 2007, the International Bureau of WIPO, 34, chemin des Colombettes, 1211 Geneva 20, Switzerland.

Woodward, M., International Search Report and Written Opinion of the International Searching Authority, PCT/US06/09082, Jul. 20, 2006, ISA/US, Commissioner for Patents, P.O. Box 1450, Alexandria Virginia 22313-1450.

Menon, K.V, et al., Severe Cholestatic Hepatitis from Troglitazone in a Patient with Nonalcoholic Steatohepatitis and Diabetes Mellitus, The American J. of Gastroenterology, 96 (5) 1631-34 (2001).

Rote Liste, No. 11081 the Medicament Mediabet of MEDICE, Chem.-Pharm. Fabrik Putter GmbH & Co. KG, Kuhloweg 37-39 Iserlohn/Germany, Editio Cantor Verlag fu Medizin and Naturwissenschaften GmbH, 1993.

Saini, "Management guidelines for use of oral hypoglycemic agents (OHA) in complex clinical situation and important drug interactions with OHA's", Int'l Journal of Diabetes in Developing Countries, 11:23-24 (1991).

Bailey et al., "Metformin", The New England Journal of Medicine, 334 (9): 574-579 (1996).

Stumvoll et al., "Metabolic Effects of Metformin in Non-Insulin Dependent Diabetes Mellitus", The New England Journal of Medicine, 333 (9): 550-554 (1995).

Reaven et al., "Measurement of Plasma Glucose, Free Fatty Acid, Lactate, and Insulin for 24 hours in Patients, with NIDDM", Diabetes, 37:1020-1024 (1988).

Boden et al.,"Evidence for a Circadian Rhythm of Insulin Sensitivity in Patients with NIDDM Caused by Cyclic Changes in Hepatic Glucose Production", Diabetes, 45: 1044-1050 (1996).

Sohda et al., "Studies on Antidiabetic Agents III. 5-Arylthiazolidine-2,4-diones as Potent Aldose Reductase Inhibitors", Chem Pharm. Bull. vol. 30, No. 10, pp. 3601-3616 (1982).

Hoffman et al., "New Oral Thiazolidinedione Antidiabetic Agents Act as Insulin Sensitizers", 15 (8) Diabetes Care, pp. 1075-1078 (Aug. 1992).

Kuzuya et al., A pilot Clinical Trial of a New Oral Hypoglycemic Agent, CS-045, in Patients with Non-Insulin Dependent Diabetes Mellitus, 11 Diabetes Research And Clinical Practice, pp. 147-154 (1991).

Gimenez Miralles, J., Supplementary European Search Report issued in EP 04 71 0656, Munich, European Patent Office, 80298 Munich, Germany, Dec. 13, 2011. This European application is related to the present application.

Cantello et al., "[[w-(Heterocyclylamino)alkoxy]benzyl]-2,4-thiazolidinediones as Potent Antihyperglycemic Agents", 37 (23) J. Med. Chem., pp. 3977-3985 (1994).

Oakes et al., "A New Antidiabetic Agent, BRL49653, Reduces Lipid Availability and Improves Insulin Action and Glucoregulation in the Rat", 43 (10) Diabetes, pp. 1203-1210 (Oct. 1994).

Drug Facts and Comparisons, pp. 635-642 (1999) published by Facts and Comparisons, St. Louis Missouri.

Physicians' Desk Reference, Glucophage, 53rd Ed., pp. 833-837 (1999).

Physicians' Desk Reference, Glucophage, 50rd Ed., pp. 752-757 (1996).

Chiao, "Sustained release drug delivery systems, Remington: The Science and Practice of Pharmacy", pp. 1660-1669 (1995).

Kong, Notice of Paragraph IV Certification Letter for Actoplus MET(R) XR, dated Nov. 21, 2011.

Hotta, N, Diabetes Update, No. 10, Kashikojima Seminar, pp. 68-77 (1994) (and English translation), Japanese document and English translation considered and attached with Notice of Allowance.

* cited by examiner

PHARMACEUTICAL FORMULATION CONTAINING A BIGUANIDE AND A THIAZOLIDINEDIONE DERIVATIVE

This application is a continuation of U.S. patent application Ser. No. 10/664,803 filed on Sep. 19, 2003 now U.S. Pat. No. 7,785,627 which claims the benefit of U.S. Provisional Patent Application Ser. No. 60/412,180 filed on Sep. 20, 2002 and U.S. Provisional Patent Application Ser. No. 60/412,181 filed on Sep. 20, 2002.

BACKGROUND OF THE INVENTION

The present invention relates to a pharmaceutical dosage form comprising an antihyperglycemic drug, in combination with a thiazolidinedione derivative. More specifically, the present invention relates to an oral dosage form comprising a biguanide e.g. metformin or buformin or a pharmaceutically acceptable salt thereof e.g., metformin hydrochloride or the metformin salts described in U.S. Pat. Nos. 3,957,853 and 4,080,472 which are incorporated herein by reference in combination with a thiazolidinedione derivative as described in U.S. Pat. No. 4,687,777 also incorporated herein by reference.

Many techniques have been used to provide controlled and extended-release pharmaceutical dosage forms in order to maintain therapeutic serum levels of medicaments and to minimize the effects of missed doses of drugs caused by a lack of patient compliance.

For example, extended release tablets have been described which have an osmotically active drug core surrounded by a semi-permeable membrane. These tablets function by allowing the aqueous components of a fluid such as gastric or intestinal fluid to permeate the coating membrane and dissolve the active ingredient so the resultant drug solution can be released through a passageway in the coating membrane. Alternatively, if the active ingredient is insoluble in the permeating fluid, it can be pushed through the passageway by an expanding agent such as a hydrogel. Some representative examples of these osmotic tablet systems can be found in U.S. Pat. Nos. 3,845,770; 3,916,899; 4,034,758; 4,077,407 and 4,783,337. U.S. Pat. No. 3,952,741 teaches an osmotic device wherein the active agent is released from a core surrounded by a semipermeable membrane only after sufficient pressure has developed within the membrane to burst or rupture the membrane at a weak portion of the membrane.

The basic osmotic device described in the above cited patents have been refined over time in an effort to provide greater control of the release of the active ingredient. For example, U.S. Pat. Nos. 4,777,049 and 4,851,229 describe osmotic dosage forms comprising a semipermeable wall surrounding a core. The core contains an active ingredient and a modulating agent wherein the modulating agent causes the active ingredient to be released through a passageway in the semipermeable membrane in a pulsed manner. Further refinements have included modifications to the semipermeable membrane surrounding the active core such as varying the proportions of the components that form the membrane, e.g. U.S. Pat. Nos. 5,178,867, 4,587,117 and 4,522,625 or increasing the number of coatings surrounding the active core, e.g. U.S. Pat. Nos. 5,650,170 and 4,892,739.

Certain controlled or sustained release formulations that employ antihyperglycemic drugs such as metformin hydrochloride have been limited to the use of an expanding or gelling agent to control the release of the drug from the dosage form. This limited research is exemplified by the teachings of WO 96/08243 and by the GLUCOPHAGE™ XR product insert which is a controlled release metformin HCl product commercially available from Bristol-Myers Squibb Co.

Thiazolidinedione derivatives have been described in U.S. Pat. No. 4,687,777. The therapeutic value of these compounds in combination therapy has further been described in U.S. Pat. Nos. 5,859,037; 5,952,356; 5,965,584; 6,150,384 and 6,172,090. However, none of these patents describe a dosage form having the advantages of the subject invention.

Pharmaceutical dosage forms containing combinations of antihyperglycemic drugs and thiazolidinedione derivatives have been proposed in the art. For example, EPO 0 749 751 (which is incorporated herein by reference) teaches pharmaceutical compositions comprising an insulin sensitivity enhancer, which could be a thiazolidinedione compound, in combination with other antidiabetics. More specifically, EPO 0 749 751 teaches that the preferred insulin sensitivity enhancer is pioglitazone, which can be combined with other antidiabetics such as metformin, phenformin or buformin, and further that these drugs can be associated (mixed and/or coated) with conventional excipients to provide taste masking or sustained release. Another example of a combination of antihyperglycemic drugs and thiazolidinedione derivatives is U.S. Pat. No. 6,011,049, (which is incorporated herein by reference). This patent teaches a single pharmaceutical composition that contains pioglitazone or troglitazone and metformin in slow release forms such as osmotic pumps or skin patches. Other combinations of antihyperglycemic drugs and thiazolidinedione derivatives can be found in U.S. Pat. Nos. 6,524,621; 6,475,521; 6,451,342 and 6,153,632 and PCT patent applications WO 01/35940 and WO 01/35941, which are incorporated herein by reference.

Also known in the art is WO 99/47125 and U.S. Pat. No. 6,099,862 that disclose a metformin osmotic tablet coated with an immediate release coating containing an antihyperglycemic or an hypoglycemic drug.

Although the prior art teaches pharmaceutical dosage formulations that contain both an antihyperglycemic compound and thiazolidinedione derivatives, the present invention provides numerous benefits over the prior art teachings as will be described below.

It is an object of the present invention to provide a dosage form comprising a first active drug, which is formulated to provide a controlled or sustained release delivery. Preferably, the first active drug is an antihyperglycemic compound. The present invention further provides for a second active drug which preferably is a thiazolidinedione derivative. The novel dosage form described herein provides for delivery of first and second active drugs such that the bioavailability of either drug is not decreased by the presence of food.

It is a further object of the present invention to provide a dosage form, as described above, comprising delivery of a first active drug as a controlled or sustained release formulation for an antihyperglycemic compound, wherein said controlled or sustained release mechanism is not regulated by an expanding polymer, in combination with delivery of a second active drug by immediate release comprising a thiazolidinedione derivative.

It is also a further object of the present invention to provide a dosage form as described above, comprising delivery of a first active drug as a controlled or sustained release formulation for an antihyperglycemic compound in combination with delivery of a second active drug by immediate release comprising a thiazolidinedione derivative that can provide continuous and non-pulsating therapeutic levels of said antihyperglycemic drug to an animal or human in need of such treatment over a eight hour to twenty-four hour period.

It is an additional object of the present invention to provide a dosage form comprising delivery of a first active drug as a controlled or sustained release formulation for an antihyperglycemic compound in combination with delivery of a second active drug by immediate release comprising a thiazolidinedione derivative that obtains peak plasma levels of the antihyperglycemic compound approximately 8-12 hours after administration and peak plasma levels of thiazolidinedione derivative approximately 1-4 hours after dosing.

It is also an object of the present invention to provide a dosage form comprising a first active drug as a controlled or sustained release pharmaceutical core tablet having only a homogeneous osmotic core wherein the osmotic core component may be made using ordinary tablet compression techniques.

It is an additional object of the present invention to provide a dosage form comprising delivery of a first active drug as a controlled or sustained release formulation for an antihyperglycemic compound in combination with delivery of a second active drug by immediate release comprising a thiazolidinedione derivative that obtains peak plasma levels of the antihyperglycemic compound approximately 8-12 hours after administration and peak plasma levels of thiazolidinedione derivative approximately 1-12 hours after dosing.

SUMMARY OF THE INVENTION

The present invention relates to a pharmaceutical dosage form comprising a first active drug, preferably an antihyperglycemic drug, in combination with a second active drug, preferably a thiazolidinedione derivative. More specifically, the present invention relates to an oral dosage form comprising a first active drug comprising a biguanide such as metformin or buformin or a pharmaceutically acceptable salt thereof eg., metformin hydrochloride or the metformin salts, in combination with a second active drug comprising a thiazolidinedione derivative The foregoing objectives are met by a dosage form comprising a first and second active drug, wherein the first active drug is formulated as a controlled release core, preferably an osmotic tablet, with or without a gelling or expanding polymer. The second active ingredient may be part of the controlled release core or it may preferably be combined with the controlled release core in a manner that provides for immediate release of the second active ingredient. For example, the second active ingredient can be incorporated into a semipermeable membrane that is applied to the core or the second active ingredient may be applied to a coated or uncoated controlled release core.

In one embodiment the second active drug, which may be the thiazolidinedione derivative, is provided as an immediate release formulation in the dosage form whereas the antihyperglycemic component is provided as a controlled release formulation in the dosage form. This immediate release portion of the formulation should provide peak plasma levels ($T_{max}$) of 1-12 hours preferably, 1-4 hours of the thiazolidinedione derivative, while the controlled release portion of the formulation may provide peak plasma levels ($T_{max}$) of 8-12 hours of the antihyperglycemic component.

Preferably, the dosage form according to the subject invention may be administered once a day, preferably with or after a meal, and most preferably with or after the evening meal. The subject dosage form can provide therapeutic levels of the drug throughout the day with peak plasma levels ($T_{max}$) of the antihyperglycemic drug being obtained between 8-12 hours after administration.

DETAILED DESCRIPTION OF THE INVENTION

The subject invention concerns a pharmaceutical formulation or dosage form comprising a first active drug comprising an antihyperglycemic drug in combination with a second active drug comprising a thiazolidinedione derivative. Preferably, the antihyperglycemic drug is a biguanide e.g. metformin or buformin or a pharmaceutically acceptable salt thereof. The antihyperglycemic drug is delivered in a controlled release manner from a tablet core, preferably an osmotic tablet core with or without a gelling or swelling polymer. The tablet core should include the antihyperglycemic drug and at least one pharmaceutically acceptable excipient. In one embodiment of the present invention the tablet core includes the antihyperglycemic drug, a binding agent and an absorption enhancer, and the tablet core is preferably coated with a polymeric coating to form a semi-permeable membrane around the tablet and drilled to create one passageway on each side of the membrane. The second active drug comprises a thiazolidinedione derivative, and is preferably applied to the membrane of the tablet core and provides for either immediate or controlled release of said thiazolidinedione derivative.

The term, antihyperglycemic drugs as used in this specification, refers to drugs that are useful in controlling or managing noninsulin-dependent diabetes mellitus (NIDDM). Antihyperglycemic drugs include the biguanides such as metformin, phenformin or buformin or the like, and pharmaceutically acceptable salts, isomers or derivatives thereof.

The term thiazolidinedione derivative as used in this specification refers to drugs that are useful for controlling or managing NIDDM. These include, but are not limited to, troglitazone, rosiglitazone, pioglitazone, ciglitazone or the like, and pharmaceutically acceptable salts, isomers or derivatives thereof.

The term binding agent refers to any conventionally known pharmaceutically acceptable binder such as polyvinyl pyrrolidone, hydroxypropyl cellulose, hydroxyethyl cellulose, hydroxypropyl methylcellulose, ethylcellulose, polymethacrylate, polyvinylalcohol, waxes and the like. Mixtures of the aforementioned binding agents may also be used. The preferred binding agents are water soluble materials such as polyvinyl pyrrolidone having a weight average molecular weight of 25,000 to 3,000,000. The binding agent may comprise approximately about 0 to about 40% of the total weight of the core and preferably about 3% to about 15% of the total weight of the core. In one embodiment, the use of a binding agent in the core is optional.

In a preferred embodiment, the core may optionally comprise an absorption enhancer. The absorption enhancer can be any type of absorption enhancer commonly known in the art such as a fatty acid, a surfactant, a chelating agent, a bile salt or mixtures thereof. Examples of some preferred absorption enhancers are fatty acids such as capric acid, oleic acid and their monoglycerides, surfactants such as sodium lauryl sulfate, sodium taurocholate and polysorbate 80, chelating agents such as citric acid, phytic acid, ethylenediamine tetraacetic acid (EDTA) and ethylene glycol-bis(β-aminoethyl ether)-N,N,N,N-tetraacetic acid (EGTA). The core may comprise approximately 0 to about 20% of the absorption enhancer based on the total weight of the core and most preferably about 2% to about 10% of the total weight of the core.

In one embodiment of the present invention, which does not employ a gelling or swelling polymer, the core of the present invention is preferably formed by granulating an antihyperglycemic drug with a binding agent and compressing the granules with the addition of a lubricant and absorption enhancer into a tablet. The core may also be formed by dry granulating the core ingredients by passing them through a roller compactor and compressing the granules with the addition of a lubricant into tablets. Direct compression may also be employed for tabletting. Other commonly known granulation procedures are known in the art. Additionally, other excipients such as lubricants, pigments or dyes may also be employed in the formulation of the subject invention.

The term gelling or swelling polymer refers to polymers that gel, swell or expand in the presence of water or biological fluids. Representative examples of gelling or swelling polymers are high molecular weight hydroxypropyl methylcellulose (such as METHOCEL® K100M, which is commercially available from Dow Chemical) and high molecular weight polyethylene oxides (such as POLYOX WSR 301, WSR 303 or WSR COAGULANT). Other gelling or swelling polymers are described in U.S. Pat. No. 4,522,625 (which is incorporated herein by reference).

The core formed as described herein, can be coated with a membrane, preferably a semipermeable polymeric coating. The semipermeable membrane is permeable to the passage of an external fluids such as water or aqueous biological fluids and is impermeable to the passage of the antihyperglycemic drug in the core. Materials that are useful in forming the semipermeable membrane are ethylcellulose, cellulose esters, cellulose diesters, cellulose triesters, cellulose ethers, cellulose ester-ether, cellulose acylate, cellulose diacylate, cellulose triacylate, cellulose acetate, cellulose diacetate, cellulose triacetate, cellulose acetate propionate and cellulose acetate butyrate. Other suitable polymers are described in U.S. Pat. Nos. 3,845,770; 3,916,899; 4,008,719; 4,036,228 and 4,612,008 (which are incorporated herein by reference). The most preferred semipermeable membrane material is cellulose acetate comprising an acetyl content of 39.3 to 40.3%, and is commercially available from Eastman Fine Chemicals.

In an alternative embodiment, the semipermeable membrane can include one of the above-described polymers and a flux-enhancing agent. The flux enhancing agent can increase the volume of fluid imbibed into the core to enable the dosage form to dispense substantially all of the antihyperglycemic drug through the passageway and/or the porous membrane. The flux-enhancing agent can be a water-soluble material or an enteric material. Examples of the preferred materials that are useful as flux enhancers are sodium chloride, potassium chloride, sucrose, sorbitol, mannitol, polyethylene glycol (PEG), propylene glycol, hydroxypropyl cellulose, hydroxypropyl methylcellulose, hydroxypropyl methylcellulose phthalate, cellulose acetate phthalate, polyvinyl alcohols, methacrylic acid copolymers, poloxamers (such as LUTROL F68, LUTROL F127, LUTROL F108 which are commercially available from BASF) and mixtures thereof. A preferred flux-enhancer is PEG 400.

The flux enhancer may also be a drug that is water soluble such as metformin or its pharmaceutically acceptable salts, or the flux enhancer may be a drug that is soluble under intestinal conditions. If the flux enhancer is a drug, the present dosage form has the added advantage of providing an immediate release of the drug, that has been selected as the flux enhancer.

The flux enhancing agent comprises approximately 0 to about 40% of the total weight of the coating, most preferably about 2% to about 20% of the total weight of the coating. The flux enhancing agent dissolves or leaches from the semipermeable membrane to form paths in the semipermeable membrane which enables fluid to enter the core and dissolve the active ingredient.

The semipermeable membrane may also be formed using a commonly known excipient such as a plasticizer. Some commonly known plasticizers include adipate, azelate, enzoate, citrate, stearate, isoebucate, sebacate, triethyl citrate, tri-n-butyl citrate, acetyl tri-n-butyl citrate, citric acid esters, and those described in the Encyclopedia of Polymer Science and Technology, Vol. 10 (1969), published by John Wiley & Sons. The preferred plasticizers are triacetin, acetylated monoglyceride, grape seed oil, olive oil, sesame oil, acetyltributylcitrate, acetyltriethylcitrate, glycerin sorbitol, diethyloxalate, diethylmalate, diethylfumarate, dibutylsuccinate, diethylmalonate, dioctylphthalate, dibutylsebacate, triethylcitrate, tributylcitrate, glyceroltributyrate and the like. Depending on the particular plasticizer, amounts from about 0 to about 25%, and preferably about 2% to about 15% of the plasticizer can be used based upon the total weight of the coating.

Generally, the membrane coating around the core will comprise from about 1% to about 5% and preferably about 2% to about 3% based upon the total weight of the core and coating.

In a preferred embodiment, the membrane coating surrounding the core further comprises a passageway that will allow for controlled release of the drug from the core. As used herein the term passageway includes an aperture, orifice, bore, hole, weakened area or an erodible element such as a gelatin plug that erodes to form an osmotic passageway for the release of the antihyperglycemic drug from the dosage form. Passageways used in accordance with the subject invention are well known and are described in U.S. Pat. Nos. 3,845,770; 3,916,899; 4,034,758; 4,077,407; 4,783,337 and 5,071,607.

Independent of the antihyperglycemic is a second active drug, preferably a thiazolidinedione derivative. This second active drug may be formulated to provide an immediate release of the thiazolidinedione derivative. In one embodiment of the present invention the thiazolidinedione derivative is applied in the form of a layer to a controlled or sustained released core comprising the antihyperglycemic drug as a layer using a binder and other conventional pharmaceutical excipients such as absorption enhancers, surfactants, plasticizers, antifoaming agents and combinations of the foregoing. An absorption enhancer may be present in the thiazolidinedione derivative layer in an amount up to about 30% w/w in comparison to the weight of the thiazolidinedione derivative. A binding agent may be present in an amount up to 150% w/w of the thiazolidinedione derivative. A second active drug immediate release formulation may be incorporated into a single dosage form by coating onto the semipermeable membrane of the dosage form by conventional methods. Alternatively, it may be incorporated by any pharmaceutically acceptable method into a single dosage form with the first active drug. The incorporation of the second active drug may be performed by, but would not be limited to, the processes selected from the group consisting of drug layering, lamination, dry compression, deposition and printing.

When the thiazolidinedione derivative is coated onto a semipermeable membrane of an osmotic tablet core, the thiazolidinedione coating should be applied from a coating solution or suspension that employs an aqueous solvent, an organic solvent or a mixture of an aqueous and an organic solvent. Typical organic solvents include acetone, isopropyl alcohol, methanol and ethanol. If a mixture of aqueous and organic solvents is employed, the ratio of water to organic solvent should range from 98:2 to 2:98, preferably 50:50 to 2:98. If a mixed solvent system is employed, the amount of binder required for coating the thiazolidinedione derivative onto the semipermeable membrane may be reduced. For example, successful coatings have been obtained from a mixed solvent system where the ratio of binder to thiazolidinedione derivative is 1:9 to 1:11. Although acceptable coatings can be obtained when the thiazolidinedione coat is applied directly to the semipermeable, a preferred approach is to first coat the semipermeable membrane with a seal coat prior to the application of the thiazolidinedione coating. As used herein a seal coat is a coating that does not contain an active pharmaceutical ingredient and that rapidly disperses or dissolves in water.

The thiazolidinedione coating solution or suspension may also contain a surfactant and a pore forming agent. A pore forming is preferably a water-soluble material such as sodium chloride, potassium chloride, sucrose, sorbitol, mannitol, polyethylene glycol (PEG), propylene glycol, hydroxypropyl cellulose, hydroxypropyl methylcellulose, hydroxypropyl methylcellulose phthalate, cellulose acetate phthalate, polyvinyl alcohols, methacrylic acid copolymers, poloxamers (such as LUTROL F68, LUTROL F127, LUTROL F108 which are commercially available from BASF) and mixtures thereof.

In an alternative embodiment, the dosage form of the present invention may also comprise an effective immediate release amount of the antihyperglycemic drug. The effective immediate release amount of antihyperglycemic drug may be coated onto the semipermeable membrane of the dosage form or it may be incorporated into the semipermeable membrane.

In addition, various diluents, excipients, lubricants, dyes, pigments, dispersants, etc., which are disclosed in Remington's Pharmaceutical Sciences (1995), may be used to optimize the above listed formulations of the subject invention.

Biguanides, such as metformin are commonly administered in dosage forms containing 500 mg, 750 mg, 850 mg, and 1000 mg. Thiazolidinedione derivatives, for example pioglitazone, are commonly administered in dosage forms containing 15 mg, 30 mg and 45 mg. The present invention is intended to encompass the above listed therapeutic combinations, without providing a specific example of each possible combination of compounds and their respective dosage amounts.

A preferred embodiment the dosage form will have the following composition:

| FIRST ACTIVE DRUG | | |
|---|---|---|
| Core: | Amount (% of core) | |
| drug | 50-98% | (75-95% preferred) |
| binder | 0.1-40% | (3-15% preferred) |
| absorption enhancer | 0-20% | (2-10% preferred) |
| lubricant | 0-5% | (0.5-1% preferred) |
| Coating: | Amount (% of coating) | |
| Semi-permeable polymer | 50-99% | (75-95% preferred) |
| flux enhancer | 0-40% | (2-20% preferred) |
| plasticizer | 0-25% | (2-15% preferred) |

| SECOND ACTIVE DRUG | Amount (% of total dosage form) | |
|---|---|---|
| drug | 0.1-20% | (1-10% preferred) |
| binder | 0.1-30% | (1-15% preferred) |
| surfactant | 0-20% | (0.1-15% preferred) |
| pore former | 0-25% | (0.1-15% preferred) |
| polymer (optional) | 0-30% | (0.1-20% preferred) |

The dosage forms prepared according to the present invention exhibit the following dissolution profile when tested in a USP Type 2 apparatus at 75 rpm in 900 ml of simulated intestinal fluid (pH 7.5 phosphate buffer) and at 37° C.:

| Release of First Active Drug | | |
|---|---|---|
| Time (hours) | % release | |
| 2 | 0-25% | (0-15% preferred) |
| 4 | 10-45% | (20-40% preferred) |
| 8 | 30-90% | (45-90% preferred) |
| 12 | NLT 50% | (NLT 60% preferred) |
| 16 | NLT 60% | (NLT 70% preferred) |
| 20 | NLT 70% | (NLT 80% preferred) |

NLT = NOT LESS THAN

| Release of Second Active Drug | | |
|---|---|---|
| Time (hours) | % release | |
| 0.5 | NLT 60% | (NLT 75% preferred) |

EXAMPLES

The following are provided by way of example only and are in no means intended to be limiting.

Example 1

A controlled release tablet containing 850 mg of metformin HCl and 15 mg pioglitazone is prepared as follows:

| First Active Drug | | |
|---|---|---|
| I. Core | (% composition of core) | |
| Metformin HCl | 90.54% | |
| Povidone K-30[1], USP | 4.38% | |
| Sodium Tribasic Phosphate | 4.58% | |
| Magnesium stearate | 0.5% | |

[1]approximate molecular weight = 50,000; dynamic viscosity (10% w/v solution at 20° C.) = 5.5-8.5 m Pa s.

(a) Granulation

The metformin HCl is delumped by passing it through a 40 mesh screen and collecting it in a clean, polyethylene-lined container. The povidone, K-30, and sodium tribasic phosphate are dissolved in purified water. The delumped metformin HCl is then added to a top-spray fluidized bed granulator and granulated by spraying the binding solution of povidone and sodium tribasic phosphate under the following conditions: inlet air temperature of 50-70° C.; atomization air pressure of 1-3 bars and spray rate of 10-100 ml/min.

Once the binding solution is depleted, the granules are dried in the granulator until the loss on drying is less than 2%.

The dried granules are passed through a comil equipped with the equivalent of an 18 mesh screen.

(b) Tableting

The magnesium stearate is passed through a 40 mesh stainless steel screen and blended with the metformin HCl granules for approximately five (5) minutes. After blending, the granules are compressed on a rotary press fitted with 15/32" round standard concave punches (plain lower punch, upper punch with an approximately 1 mm indentation pin).

As stated above, the orifice may be formed by any means commonly employed in the pharmaceutical industry.

(c) Seal Coating (optional)

The core tablet can be seal coated with an Opadry material or other suitable water-soluble material by first dissolving the Opadry material, preferably Opadry Clear, in purified water. The Opadry solution is then sprayed onto the core tablet using a pan coater under the following conditions: exhaust air temperature of 38-42° C.; atomization pressure of 28-40 psi and spray rate of 10-15 ml/min. The core tablet is coated with the sealing solution until a theoretical coating level of approximately 2-4% is obtained.

| II | Semi-Permeable Membrane | (% composition of membrane) |
|---|---|---|
| | Cellulose Acetate (398-10)[2] | 85% |
| | Triacetin | 5% |
| | PEG 400 | 10% |

[2]acetyl content 39.3-40.3%

(a) Semi-Permeable Membrane Coating Process

The cellulose acetate is dissolved in acetone while stirring with a homogenizer. The polyethylene glycol 400 and triacetin are added to the cellulose acetate solution and stirred until a clear solution is obtained. The clear coating solution is then sprayed onto the seal coated tablets in a fluidized bed coater employing the following conditions: product temperature of 16-22° C.; atomization pressure of approximately 3 bars and spray rate of 120-150 ml/min. The sealed core tablet is coated until a theoretical coating level of approximately 3% is obtained.

| III. | Second Active Drug Layering | (% composition of second component) |
|---|---|---|
| | Pioglitazone HCl | 43.5% |
| | Tween 80 | 2.0% |
| | Hydroxypropyl methylcellulose | 54.5% |

Tween 80 and hydroxypropyl methylcellulose are dissolved in purified water. Pioglitazone HCl is then dispersed into this solution. The resulting suspension is then sprayed onto the above-described tablets.

Example 2

A controlled release tablet containing 850 mg of metformin HCl and 15 mg pioglitazone is prepared as follows:

| | First Active Drug | |
|---|---|---|
| I. | Core | (% composition of core) |
| | Metformin HCl | 88.555% |
| | Povidone K-90[3], USP | 6.368% |
| | Sodium Lauryl Sulfate | 4.577% |
| | Magnesium Stearate | 0.5% |

[3]approximate molecular weight = 1,000,000, dynamic viscosity (10% w/v solution at 20° C. = 300-700 m Pa s.

(a) Granulation

The metformin HCl and sodium lauryl sulfate are delumped by passing them through a 40 mesh screen and collecting them in a clean, polyethylene-lined container. The povidone, K-90, is dissolved in purified water. The delumped metformin HCl and sodium lauryl sulfate are then added to a top-spray fluidized bed granulator and granulated by spraying with the binding solution of povidone under the following conditions: inlet air temperature of 50-70° C.; atomization air pressure of 1-3 bars and spray rate of 10-100 ml/min.

Once the binding solution is depleted, the granules are dried in the granulator until the loss on drying is less than 2%. The dried granules are passed through a comil equipped with the equivalent of an 18 mesh screen.

(b) Tableting

The magnesium stearate is passed through a 40 mesh stainless steel screen and blended with the metformin HCl granules for approximately five (5) minutes. After blending, the granules are compressed on a rotary press fitted with 15/32" round standard concave punches (plain lower punch, upper punch with an approximately 1 mm indentation pin).

As stated above, the orifice may be formed by any means commonly employed in the pharmaceutical industry.

(c) Seal Coating (optional)

The core tablet can be seal coated with an Opadry material or other suitable water-soluble material by first dissolving the Opadry material, preferably Opadry Clear in purified water. The Opadry solution is then sprayed onto the core tablet using a pan coater under the following conditions: exhaust air temperature of 38-42° C.; atomization pressure of 28-40 psi and spray rate of 10-15 ml/min. The core tablet is coated with the sealing solution until a theoretical coating level of approximately 2% is obtained.

| II | Semi-Permeable Membrane | (% composition of membrane) |
|---|---|---|
| | Cellulose Acetate (398-10)[4] | 85% |
| | Triacetin | 5% |
| | PEG 400 | 10% |

[4]acetyl content 39.3-40.3%

(a) Semi-Permeable Membrane Coating Process

The cellulose acetate is dissolved in acetone while stirring with a homogenizer. The polyethylene glycol 400 and triacetin are added to the cellulose acetate solution and stirred. The coating solution is then sprayed onto the seal coated tablets in a fluidized bed coater employing the following conditions: product temperature of 16-22° C.; atomization pressure of approximately 3 bars and spray rate of 120-150 ml/min. The sealed core tablet is coated until a theoretical coating level of approximately 3% is obtained.

| III. Second Active Drug Layering | (% composition of second component) |
|---|---|
| Pioglitizone HCl | 43.5% |
| Tween 80 | 2.0% |
| Hydroxypropyl methylcellulose | 54.5% |

Tween 80 and hydroxypropyl methylcellulose are dissolved in purified water. Pioglitazone HCl is then dispersed into this solution. The resulting suspension is then sprayed onto the above described tablets.

Example 3

A controlled release tablet containing 500 mg of metformin HCl and 15 mg pioglitazone is prepared as follows:
I. First Active Drug A 500 mg osmotic tablet is prepared as described in Example 2 above except a compound cup is used during tableting. The 500 mg osmotic tablet has the following composition:

| CORE | |
|---|---|
| Metformin HCl | 500 mg/tablet |
| Povidone K-90, USP | 35.96 mg/tablet |
| Sodium lauryl sulfate, NF | 25.84 mg/tablet |
| Magnesium stearate, NF | 2.82 mg/tablet |
| SEAL COATING | |
| Opadry Clear (YS-1-7006) | 23.53 mg/tablet |
| SR COATING | |
| Cellulose Aacetate, 398-10, NF | 23.56 mg/tablet |
| Triacetin, USP | 1.39 mg/tablet |
| Polyethylene Glycol 400, NF | 2.77 mg/tablet |
| Total weight | 615.87 mg/tablet |

II. Second Active Drug Layering

An immediate release amount of pioglitazone HCL is applied to the 500 mg metformin HCl core tablet prepared in step I. The final tablet has the following composition:

| Metformin HCl osmotic tablet | 615.87 mg/tablet |
|---|---|
| Pioglitazone Coating | |
| Pioglitazone HCl | 16.53 mg/tablet |
| Tween 80 | 2.0 mg/tablet |
| Polyplasdone XL | 15.0 mg/tablet |
| Opadry Clear (YS-1-7006) | 8.47 mg/tablet |
| Color Coating | |
| Opadry White | 10.0 mg/tablet |
| Polishing Coat | |
| Candelilla Wax Powder | 2.0 mg/tablet |

The pioglitazone coating is directly applied to the 500 mg metformin HCl osmotic tablets. The pioglitazone coating is prepared by dissolving 0.252 kg of Opadry Clear, 0.269 kg of Polyplasdone XL and 0.036 kg of Tween 80 in 9.908 kg of purified water using a homogenizer. Once these ingredients are dissolved, 0.296 kg of pioglitazone HCl is dispersed into the solution and homogenized. The homogenized dispersion is then directly applied to the 500 mg metformin HCl osmotic tablets using a 24"O'Hara Labcoat III pan coater with the following conditions:

| Spray Rate | 15-27 ml/min |
|---|---|
| Exhaust Temperature | 42-47° C. |
| Nozzle Pressure | 25 psi |
| Pan Speed | 5-9 rpms |
| Inlet Air Flow | 300-400 CFM. |

Once the pioglitazone coating has been applied to the 500 mg metformin HCl osmotic tablet core, an aesthetic or color coating of Opadry white is applied to the pioglitazone coated tablet. The color coating is prepared by dispersing 0.179 kg of Opadry White in 1.791 kg of purified water. The Opadry White suspension is applied to the pioglitazone coated tablet using a 24" O'Hara Labcoat III pan coater under the following conditions:

| Spray Rate | 20-35 ml/min |
|---|---|
| Exhaust Temperature | 35-45° C. |
| Nozzle Pressure | 25 psi |
| Pan Speed | 9 rpm |
| Inlet Air Flow | 390-500 CFM |

Once the color coating is applied, the tablets are polished using 0.036 kg of Candelilla wax powder.

Example 4

A controlled release tablet containing 500 mg of metformin HCl and 15 mg pioglitazone is prepared as follows:
I. First Active Drug A 500 mg osmotic tablet is prepared as described in Example 2 above except a compound cup is used during tableting. The 500 mg osmotic tablet has the following composition:

| CORE | |
|---|---|
| Metformin HCl | 500 mg/tablet |
| Povidone K-90, USP | 35.96 mg/tablet |
| Sodium Lauryl Sulfate, NF | 25.84 mg/tablet |
| Magnesium Stearate, NF | 2.82 mg/tablet |
| SEAL COATING | |
| Opadry Clear (YS-1-7006) | 23.53 mg/tablet |
| SEMI-PERMEABLE MEMBRANE COATING | |
| Cellulose Acetate, 398-10, NF | 23.56 mg/tablet |
| Triacetin, USP | 1.39 mg/tablet |
| Polyethylene Glycol 400, NF | 2.77 mg/tablet |
| Total weight | 615.87 mg/tablet |

II. Second Active Drug Layering

An immediate release amount of pioglitazone HCL is applied to the 500 mg metformin HCl seal coated tablet prepared in Step I. The final tablet has the following composition:

| Metformin HCl osmotic tablet | 615.87 mg/tablet |
|---|---|
| Seal Coat | |
| Opadry Clear (YS-1-7006) | 13.8 mg/tablet |
| Pioglitazone Coating | |
| Pioglitazone HCl | 16.53 mg/tablet |
| Tween 80 | 2.0 mg/tablet |
| Sodium Chloride | 4.27 mg/tablet |
| Opadry Clear (YS-1-7006) | 2.0 mg/tablet |

| Color Coating | |
|---|---|
| Opadry White | 8.10 mg/tablet |
| Polishing Coat | |
| Candelilla Wax | 0.20 mg/tablet |

The seal coating solution is prepared by dissolving 0.258 kg of Opadry Clear in 2.576 kg of purified water and spraying the solution onto approximately 12.088 kg of the 500 mg cellulose acetate coated metformin HCl tablet cores using a 24" Ohara Labcoat III pan coater. The seal coat is applied to the 500 mg metformin HCl osmotic tablets under the following conditions:

| | |
|---|---|
| Spray Rate | 20-35 ml/min |
| Exhaust Temperature | 35-45° C. |
| Nozzle Pressure | 25 psi |
| Pan Speed | 9 rpm |
| Inlet Air Flow | 390-500 CFM |

The pioglitazone coating is applied to the seal coated 500 mg metformin HCl osmotic tablets. The pioglitazone coating is prepared by dissolving 0.040 kg of Opadry Clear, 0.085 kg of sodium chloride and 0.040 kg of Tween 80 in 4.915 kg of purified water using a homogenizer. Once these ingredients are dissolved, 0.328 kg of pioglitazone HCl is dispersed into the solution and homogenized. The homogenized dispersion is then applied to the seal coated 500 mg metformin HCl osmotic tablets using a 24" Ohara Labcoat III pan coater with the following conditions:

| | |
|---|---|
| Spray Rate | 10-30 ml/gun/min |
| Exhaust Temperature | 35-45° C. |
| Atomization Air Pressure | 20-40 psi |
| Pattern Air Pressure | 20-40 psi |
| Pan Speed | 8-12 rpms |
| Inlet Air Flow | 250-450 CFM. |

Once the pioglitazone coating has been applied to the seal coated 500 mg metformin HCl osmotic tablets, an aesthetic or color coating of Opadry white is applied to the pioglitazone coated tablet. The color coating is prepared by dispersing 0.159 kg of Opadry White in 1.585 kg of purified water. The Opadry White suspension is applied to the pioglitazone coated tablet using conditions similar to those described above for application of the seal coating. Once the color coating is applied, the tablets are polished using 0.004 kg of Candelilla wax powder.

Example 5

A controlled release tablet containing 1000 mg of metformin HCl and 30 mg pioglitazone is prepared as follows:

I. First Active Drug

A 1000 mg osmotic tablet is prepared as described in Example 2 above. The 1000 mg osmotic tablet has the following composition:

| CORE | |
|---|---|
| Metformin HCl | 1000 mg/tablet |
| Povidone K-90, USP | 78.0 mg/tablet |
| Sodium Lauryl Sulfate, NF | 51.69 mg/tablet |
| Magnesium Stearate, NF | 5.66 mg/tablet |
| SEAL COATING | |
| Opadry Clear (YS-1-7006) | 47.05 mg/tablet |
| SEMI-PERMEABLE MEMBRANRE COATING | |
| Cellulose Acetate, 398-10, NF | 15.77 mg/tablet |
| Triacetin, USP | 0.92 mg/tablet |
| Polyethylene Glycol 400, NF | 1.85 mg/tablet |
| Total weight | 1201.0 mg/tablet |

II. Second Active Drug

An immediate release amount of pioglitazone HCL is applied to the 1000 mg metformin HCl tablets prepared in step I. The final tablet has the following composition:

| | |
|---|---|
| Metformin HCl osmotic tablet | 1201.0 mg/tablet |
| Seal Coating | |
| Opadry Clear (YS-1-7006) | 16.0 mg/tablet |
| Pioglitazone Coating | |
| Pioglitazone HCl | 33.06 mg/tablet |
| Sodium Chloride | 4.27 mg/tablet |
| Opadry Clear (YS-1-7006) | 3.0 mg/tablet |
| Color Coating | |
| Opadry II White | 20.27 mg/tablet |
| Polishing Coat | |
| Candelilla Wax Powder | 0.40 mg/tablet |

The seal coating is prepared by dispersing 0.174 kg of Opadry Clear in 3.478 kg of ethanol and mixing the dispersion for 15 minutes. The dispersion is then sprayed onto approximately 13.174 kg of 1000 mg metformin HCl cellulose acetate coated tablets using a 24" O'Hara Labcoat III pan coater. The seal coat is applied to the 1000 mg metformin HCl cellulose acetate coated osmotic tablets with the following conditions:

| | |
|---|---|
| Spray Rate | 10-30 ml/gun/min |
| Exhaust Temperature | 25-45° C. |
| Atomization Air Pressure | 20-40 psi |
| Pan Speed | 6-12 rpms |
| Pattern Air Pressure | 20-40 psi |
| Inlet Air Flow | 250-450 CFM |

The pioglitazone coating then is applied to the seal coated 1000 mg metformin HCl osmotic tablets. The pioglitazone coating is prepared by dissolving 0.036 kg of Opadry Clear and 0.046 kg of sodium chloride in 5.344 kg of ethanol using a homogenizer. Once the ingredients are dispersed, 0.359 kg of pioglitazone HCl is dispersed into the solution and homogenized. The homogenized dispersion is then applied to the seal coated 1000 mg metformin HCl cellulose acetate coated tablets using a 24" O'Hara Labcoat III pan coater with the following conditions:

| | |
|---|---|
| Spray Rate | 10-30 ml/gun/min |
| Exhaust Temperature | 25-45° C. |
| Atomization Air Pressure | 20-40 psi |
| Pan Speed | 6-12 rpm |
| Pattern Air Pressure | 20-40 psi |
| Inlet Air Flow | 250-450 CFM |

Once the pioglitazone coating has been applied, an aesthetic or color coating of Opadry II White is applied to the pioglitazone coated tablets. The color coating is prepared by dispersing 0.220 kg of Opadry II White in 4.407 kg of ethanol. The Opadry II White suspension is then applied to the pioglitazone HCl coated tablets using a 24" O'Hara Labcoat III pan coater using conditions similar to those described above for the seal coating. Once the color coating is applied, the tablets are polished using 0.004 kg of Candelilla wax powder.

Example 6

A controlled release tablet containing 1000 mg of metformin HCl and 30 mg pioglitazone is prepared as follows:

I. First Active Drug

A 1000 mg osmotic tablet is prepared as described in Example 2 above. The 1000 mg osmotic tablet has the following composition:

| CORE | |
|---|---|
| Metformin HCl | 1000 mg/tablet |
| Povidone K-90, USP | 78.0 mg/tablet |
| Sodium Lauryl Sulfate, NF | 51.69 mg/tablet |
| Magnesium Stearate, NF | 5.65 mg/tablet |
| SEAL COATING | |
| Opadry Clear (YS-1-7006) | 47.05 mg/tablet |
| SEMI-PERMEABLE MEMBRANE COATING | |
| Cellulose Acetate, 398-10, NF | 15.77 mg/tablet |
| Triacetin, USP | 0.92 mg/tablet |
| Polyethylene Glycol 400, NF | 1.85 mg/tablet |
| Total weight | 1201.0 mg/tablet |

II. Second Active Drug

An immediate release amount of pioglitazone HCL is applied to the 1000 mg metformin HCl cellulose acetate coated tablets prepared in step I. The final tablet has the following composition:

| | |
|---|---|
| Metformin HCl osmotic tablet | 1201.0 mg/tablet |
| Seal Coat | |
| Opadry Clear (YS-1-7006) | 21.0 mg/tablet |
| Pioglitazone Coating | |
| Pioglitazone HCl | 33.06 mg/tablet |
| Sodium Chloride | 5.0 mg/tablet |
| Opadry Clear (YS-1-7006) | 3.7 mg/tablet |
| Color Coating | |
| Opadry II White (YS-22-7719) | 21.54 mg/tablet |
| Polishing Coat | |
| Candelilla Wax Powder | 0.40 mg/tablet |

The seal coat is applied to the 1000 mg metformin HCl osmotic tablet. The seal coating is prepared by dispersing 0.229 kg of Opadry Clear in 4.573 kg of alcohol USP and mixing the dispersion for 15 minutes. The dispersion is then sprayed onto approximately 13.08 kg of the 1000 mg metformin HCl tablet cores using a 24" Ohara Labcoat III pan coater with the nozzle tip set 4±2" from the top of the static bed and the following conditions:

| | |
|---|---|
| Spray Rate | 25 ± 10 ml/gun/min |
| Exhaust Temperature | 25° C. ± 5° C. |
| Atomization Pressure | 10-40 psi |
| Pan Speed | 4-9 rpm |
| Supply Air Flow | 200 ± 100 CFM |
| Pattern Air Pressure | 10-40 psi |

The seal coating dispersion is continuously stirred until it is consumed during the coating process.

The pioglitazone coating then is applied to the seal coated 1000 mg metformin HCl osmotic tablets. The pioglitazone coating is prepared by mixing 4.434 kg of alcohol USP and 1.250 kg of purified water and slowly dispersing 0.040 kg of Opadry Clear into the solvent mixture. Once the Opadry Clear is dispersed, it is homogenized for about 10 minutes. Once the Opadry Clear dispersion is homogenized, 0.054 kg of sodium chloride is added to the dispersion and homogenized for about 2 minutes. After the sodium chloride is homogenized, 0.360 kg of pioglitazone HCl is slowly dispersed into the solvent mix and then homogenized for about 10 minutes. Once the pioglitazone HCl is homogenized, the homogenizer is removed from the mixing vessel and replaced with an air mixer and mixed for an additional 15 minutes. The pioglitazone suspension is stirred until the suspension is consumed during the coating process. The pioglitazone HCl suspension is applied to the seal coated 1000 mg metformin HCl osmotic tablet cores using a 24" Ohara Labcoat III pan coater with the nozzle tip set 4±2" above the top of the static bed with the following conditions:

| | |
|---|---|
| Spray Rate | 25 ± 10 ml/gun/min |
| Exhaust Temperature | 25 ± 5° C. |
| Atomization Pressure | 10-40 psi |
| Pan Speed | 4-9 rpms |
| Pattern Air Pressure | 10-40 psi |
| Supply Air Flow | 200 ± 100 CFM |

Once the pioglitazone coating has been applied to the seal coated 1000 mg metformin HCl osmotic tablets, an aesthetic coating of Opadry II White is applied to the pioglitazone coated tablet. The aesthetic coating is prepared by dispersing 0.235 kg of Opadry II White (Y-22-7719) in 4.691 kg of alcohol USP and mixing the dispersion for about 1 hour. The Opadry II White dispersion is then sprayed onto the pioglitazone HCl coated tablets using a 24" Ohara Labcoat III pan coater with the nozzle tip set 4±2" from the top of the static bed and the following conditions:

| | |
|---|---|
| Spray Rate | 25 ± 10 ml/gun/min |
| Exhaust Temperature | 25° C. ± 5° C. |
| Atomization Pressure | 10-40 psi |
| Pan Speed | 4-9 rpm |
| Supply Air Flow | 200 ± 100 CFM |
| Pattern Air Pressure | 10-40 psi |

The color coating dispersion is continuously stirred until the dispersion is consumed during the coating process.

Once the aesthetic coating suspension is consumed, the tablets are dried in the coating pan for about 5 minutes with a pan speed of about 2-8 rpms and an exhaust temperature of 25±5° C. Once the tablets are dried, the exhaust air is turned off and the pan speed is adjusted to about 3-4 rpms and 0.004 kg of Candellia wax powder that had been passed through a 60 mesh screen is sprinkled onto the tablets. After the tablets have rolled in the wax for about 5 minutes the exhaust air is turned on and the tablets are rolled for an additional 10 minutes.

The final polished tablet exhibits the following pioglitazone HCl dissolution profile when tested in a USP apparatus type 1 at 100 rpm in a pH 2.0 HCl-0.3M KCl buffer solution:

| Time | % Pioglitazone Released |
|---|---|
| 10 min. | 42% |
| 20 min | 79% |
| 30 min | 95% |
| 45 min | 102% |

While certain preferred and alternative embodiments of the invention have been set forth for purposes of disclosing the invention, modifications to the disclosed embodiments may occur to those who are skilled in the art. Accordingly, the appended claims are intended to cover all embodiments of the invention and modifications thereof which do not depart from the spirit and scope of the invention.

What is claimed is:

1. A method for preparing a sustained release oral tablet comprising:
   a) forming a controlled release metformin hydrochloride tablet comprising 500 mg to 1000 mg of metformin;
   b) preparing an immediate release coating solution comprising:
      i) pioglitazone hydrochloride;
      ii) water;
      iii) an organic solvent selected from the group consisting of acetone, isopropyl alcohol, methanol or ethanol;
      iv) a binder;
      v) optionally a surfactant;
      vi) optionally a pore forming agent
   wherein the ratio of water to organic solvent is 50:50 to 2:98 and the ratio of binder to pioglitazone hydrochloride is 1:9 to 1:11;
   c) applying the immediate release coating solution to the controlled release metformin hydrochloride tablet so that when tested in a United States Pharmacopeia (USP) Type 2 apparatus at 75 rpm in 900 ml of simulated intestinal fluid (pH 7.5 phosphate buffer) and at 37° C., not less than 75% of the pioglitazone hydrochloride is released from the sustained release tablet in 30 minutes.

2. The method of claim 1 wherein not less than 95% of the pioglitazone hydrochloride is released from the sustained release tablet in 30 minutes.

3. The method of claim 1 wherein the sustained release tablet is prepared without a gelling polymer.

4. The method of claim 1 wherein the controlled release metformin hydrochloride tablet is formed by:
   A) mixing the metformin hydrochloride with at least one pharmaceutically acceptable excipient;
   B) compressing the mixture of step (A) into a tablet; and
   C) coating the tablet of step (B) with a membrane.

5. A tablet prepared by the method of claim 1.

6. A method for preparing a sustained release oral tablet comprising:
   i) forming a controlled release metformin hydrochloride tablet comprising 500 mg to 1000 mg of metformin and without a gelling polymer comprising the steps of:
      a) mixing the metformin hydrochloride with at least one pharmaceutically acceptable excipient;
      b) compressing the mixture of step (a) into a tablet; and
      c) coating the tablet of step (b) with a membrane;
   ii) preparing an immediate release coating solution comprising:
      a) pioglitazone hydrochloride;
      b) water;
      c) an organic solvent selected from the group consisting of acetone, isopropyl alcohol, methanol or ethanol;
      d) a binder;
      e) optionally a surfactant;
      f) optionally a pore forming agent
   wherein the ratio of water to organic solvent is 50:50 to 2:98 and the ratio of binder to pioglitazone hydrochloride is 1:9 to 1:11;
   iii) applying the immediate release coating solution to the membrane of the controlled release metformin hydrochloride tablet so that when tested in a United States Pharmacopeia (USP) Type 2 apparatus at 75 rpm in 900 ml of simulated intestinal fluid (pH 7.5 phosphate buffer) and at 37° C., not less than 95% of the pioglitazone hydrochloride is released from the sustained release tablet in 30 minutes.

7. A tablet prepared by the method of claim 6.

* * * * *